US011382900B2

(12) United States Patent
Choi et al.

(10) Patent No.: US 11,382,900 B2
(45) Date of Patent: *Jul. 12, 2022

(54) COMPOSITION FOR PREVENTING OR TREATING SLEEP DISORDERS

(71) Applicant: AMOREPACIFIC CORPORATION, Seoul (KR)

(72) Inventors: Gyeyoung Choi, Yongin-si (KR); Hyunjin Nam, Yongin-si (KR); Miyoung Park, Yongin-si (KR); Kyoungmi Jung, Yongin-si (KR); Jihae Lee, Yongin-si (KR); Chang Soon Choi, Yongin-si (KR); Youngho Park, Yongin-si (KR); Jong Hwa Roh, Yongin-si (KR); Eunsil Park, Yongin-si (KR); Jaehong Park, Yongin-si (KR); Kwanghyun Shin, Yongin-si (KR); Byoung Young Woo, Yongin-si (KR); Kiwha Lee, Yongin-si (KR); Wonkyung Cho, Yongin-si (KR); Joonho Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 240 days.

This patent is subject to a terminal disclaimer.

(21) Appl. No.: 16/805,202

(22) Filed: Feb. 28, 2020

(65) Prior Publication Data

US 2020/0197378 A1 Jun. 25, 2020

Related U.S. Application Data

(63) Continuation-in-part of application No. PCT/KR2018/004330, filed on Apr. 13, 2018.

(30) Foreign Application Priority Data

Aug. 31, 2017 (KR) ........................ 10-2017-0110629
Apr. 12, 2018 (KR) ........................ 10-2018-0042811

(51) Int. Cl.
| | | |
|---|---|---|
| *A61K 31/44* | (2006.01) | |
| *A61K 9/00* | (2006.01) | |
| *A61K 9/06* | (2006.01) | |

(52) U.S. Cl.
CPC ............ *A61K 31/44* (2013.01); *A61K 9/0014* (2013.01); *A61K 9/06* (2013.01)

(58) Field of Classification Search
CPC ......... A61K 31/44; A61K 9/0014; A61K 9/06
USPC ....................................................... 514/357
See application file for complete search history.

(56) References Cited

U.S. PATENT DOCUMENTS

2008/0312234 A1 12/2008 Kim et al.
2020/0197379 A1* 6/2020 Choi .................... A61K 9/0014

FOREIGN PATENT DOCUMENTS

| KR | 101410318 B1 | 6/2014 |
|---|---|---|
| WO | 2007047575 A2 | 4/2007 |
| WO | 2008013414 A1 | 1/2008 |

OTHER PUBLICATIONS

Sleep Disorders [online], [retrieved on Dec. 20, 2021] Retrieved from the Internet, URL: https://medlineplus.gov/sleepdisorders.html (Year: 2021).*
Jun-Won Yun et al: "Antipruritic Effects of TRPVl Antagonist in Murine Atopic Dermatitis and Itching Models", Journal of Investigative Dermatology, Jul. 1, 2011, pp. 1576-1579, vol. 131, No. 7, XP055582204, NL ISSN: 0022-202X, DOI: 10.1038/jid.2011.87.
Wilkowska, Aleksandra, Elbieta Grubska-Suchanek, and Roman Nowicki. "Evaluation of safety and efficacy of Dermaveel in treatment of atopic dermatitis.", Alergologia Polska-Polish Journal of Allergology 2, 2015, pp. 128-133.
International Search Report and Written Opinion for International application No. PCT/KR2018/004330, dated Jul. 24, 2018, 10 pages, ISA/KR.
Chang et al., Mechanism of sleep disturbance in children with atopic dermatitis and the role of the circadian rhythm and melatonin. Int'l Journal of Molecular Sciences, 2016, vol. 17(4):462.
Ozawa et al., Neuroselective transcutaneous electrical stimulation reveals neuronal sensitization in atopic dermatitis, The American Academy of Dermatology, 2009, pp. 609-614, vol. 60.
Kang-Hui Park et al., Oral and topical pharmacokinetic studies of a novel TRPV1 antagonist, PAC-14028 in rats and minipigs using liquid chromatography/tandem mass spectrometric method, Journal of Pharmaceutical and Biomedical Analysis, 2012, pp. 8-14, vol. 61.
Kung-Sen Chang et al., Atopic Dermatitis, Melatonin, and Sleep Disturbance, Pediatrics, 2014, pp. e397-e405, vol. 134.
Kyung-Min Lim et al., Development of PAC-14028, a Novel Transient Receptor Potential Vanilloid Type 1 (TRPV1) Channel Antagonist as a New Drug for Refractory Skin Diseases, Archives of Pharmacal Research. 2012. pp. 393-396, vol. 35, No. 3.
Jun-Won Yun et al., TRPV1 antagonist can suppress the atopic dermatitis-like symptoms by accelerating skin barrier recovery, Journal of Dermatological Science, 2011, pp. 8-15, vol. 62.
Jin et al., "Animal models of atopic dermatitis", Journal of Investigative Dermatology, 2009, pp. 31-40, vol. 129.
Ewald et al. "Major differences between human atopic dermatitis and murine models, as determined by using global transcriptomic profiling", J Allergy Clin Immunol. 2017, pp. 562-571, vol. 139 No. 2.
Tanaka et al., "Recent findings in mouse models for human atopic dermatitis", Japanese Association for Laboratory Animal Science, 2012, pp. 77-84, vol. 61.
Leshem et al., "What the EASI score tells US about the severity of atopic dermatitis—an interpretability study", British Journal of Dermatology, 2015, pp. 1353-1357, vol. 172.

(Continued)

*Primary Examiner* — Kristin A Vajda
(74) *Attorney, Agent, or Firm* — Lucas & Mercanti, LLP

(57) ABSTRACT

Disclosed is a method for preventing or treating sleep disorders using TRPV1 receptor antagonist, (R)—N-[1-(3,5-difluoro-4-methanesulfonylamino-phenyl)-ethyl]-3-(2-propyl-6-trifluoromethyl-pyridin-3-yl)-acrylamide. The method of the present invention can effectively and safely prevent or treat sleep disorders accompanying pruritus caused by atopic dermatitis.

8 Claims, 7 Drawing Sheets

(56) References Cited

OTHER PUBLICATIONS

Alawi et al., "The sympathetic nervous system is controlled by transient receptor potential vanilloid 1 in the regulation of body temperature", The FASEB Journal, 2015, pp. 4285-4298, vol. 29.
Ayoub et al., "Answering the burning question of how transient receptor potential vanilloid-1 channel antagonists cause unwanted hyperthermia", Pharmacological Reviews, 2009, pp. 225-227, vol. 61 No. 3.
Pasparakis et al., "Mechanisms regulating skin immunity and inflammation", Nature Reviews, May 2014, pp. 289-301, vol. 14.
Hay et al., "Clinical development success rates for investigational drugs", Nature Biotechnology, Jan. 2014, pp. 10-51, vol. 32.
Waring et al.,"An analysis of the attrition of drug candidates from four major pharmaceutical companies", Nature Reviews Drug Discovery, Jun. 2015, pp. 1-12, vol. 14.
Pang, D. J. et al., "Understanding the complexity of gammadelta Tcell subsets in mouse and human", Immunology, 2012, pp. 283-290, vol. 136.
Zollner et al., "Acute and chronic models of allergic contact dermatitis: advantages and limitations", Ernst Schering Res Found Workshop, 2005, pp. 255-275.
Tarayre et al., "Comparative actions of immunosuppressants, glucocorticoids and non-steroidal anti-inflammatory drugs on various models of delayed hypersensitivity and on a non-immune inflammation in mice", Arzneimittel-forschung, 1990.
Queille-Roussel, C. et al., "SDZ ASM 981 is the first non-steroid that suppresses established nickel contact dermatitis elicited by allergen challenge", Contact Dermatitis, 2000, pp. 349-350, vol. 42.
Byung Eui Kim et al.,"TNF-alpha downregulates filaggrin and loricrin through c-Jun N-terminal kinase: role for TNF-alpha antagonists to improve skin barrier, Journal of Investigative Dermatology", 2011, pp. 1272-1279, vol. 131.
Perera, G. K. et al., "Psoriasis," The Annual Review of Pathology: Mechanisms of Disease, 2012, pp. 385-422, vol. 7.
Wagner, E. F. et al., "Psoriasis: what we have learned from mouse models", Nature Reviews Rheumatology, 2010, 6, pp. 704-714, vol. 6.
Lee, Y.W. et al., "Efficacy and safety of PAC 14028 cream a novel, topical, nonsteroidal, selective TRPV1 antagonist in patients with mild to moderate atopic dermatitis: a phase lib randomized trial", British Journal of Dermatology, 2019, vol. 180, pp. 1030-1038.
Wohlrab, "Topical preparations and their use in dermatology", J. German Society of Dermatology, 2016, pp. 1061-1070.
Eure, "Routes of Medication Administration", 2016,. Available from: < How to Take Your Meds: Medication Administration Routes (verywellhealth.com) >.
Drug absorption through the skin: a mixed blessing, Archives of Disease in Childhood, 1987, vol. 62, pp. 220-221.
Jia, Wei, et al. "Cataplasma of traditional Chinese medicine", Zhongguo Zhong Yao Za Zhi., 2003, vol. 28 No.1, pp. 7-11.
"Healing Foot Pain with Chinese Medicine", Emily Grace Acupuncture, 2019, Available from : < Acupuncture for Plantar Fasciitis·Emily Grace Acupuncture>.

* cited by examiner

[FIG. 1A]
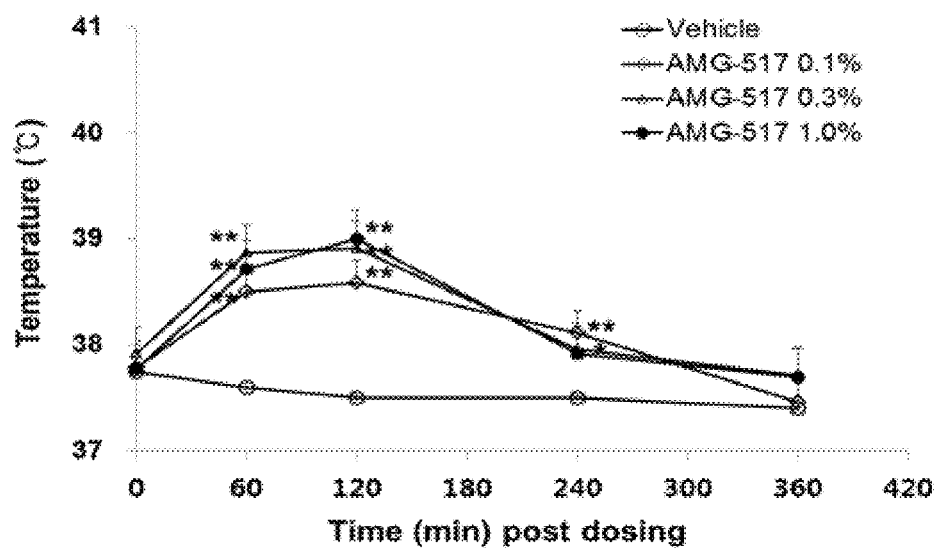
[FIG. 1B]
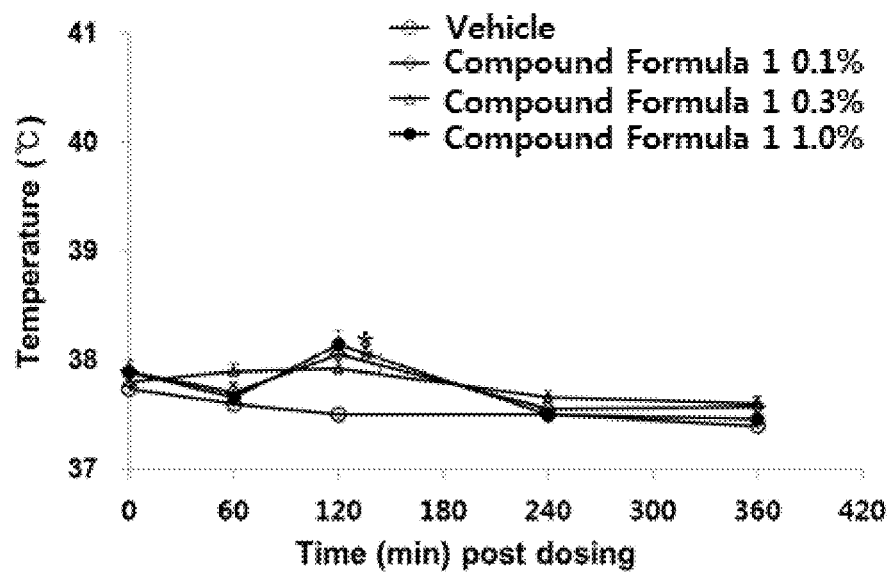

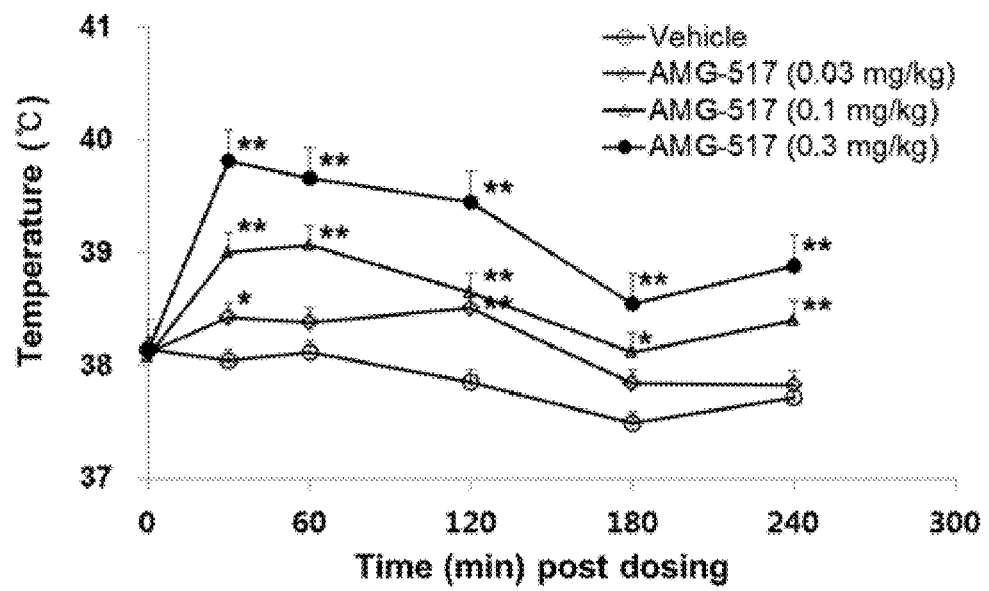
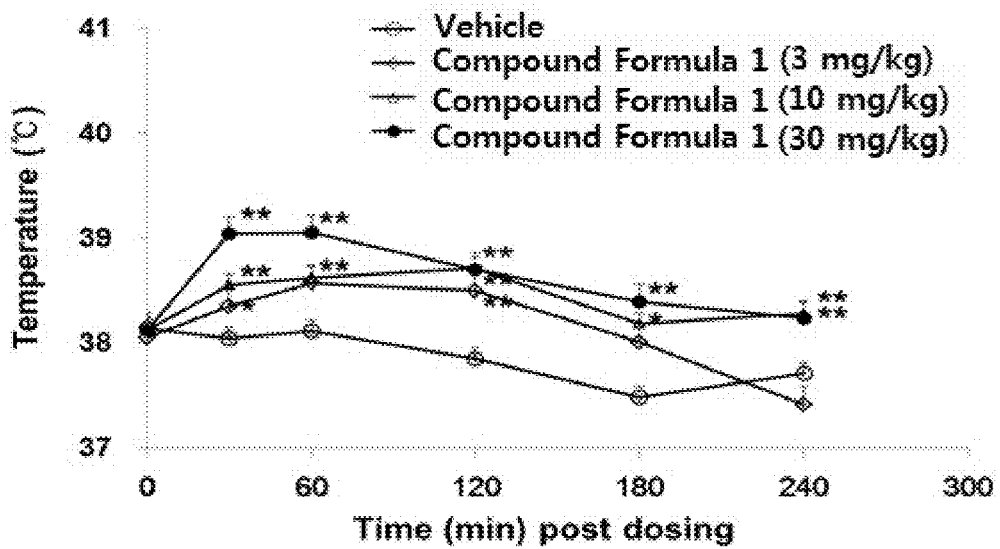

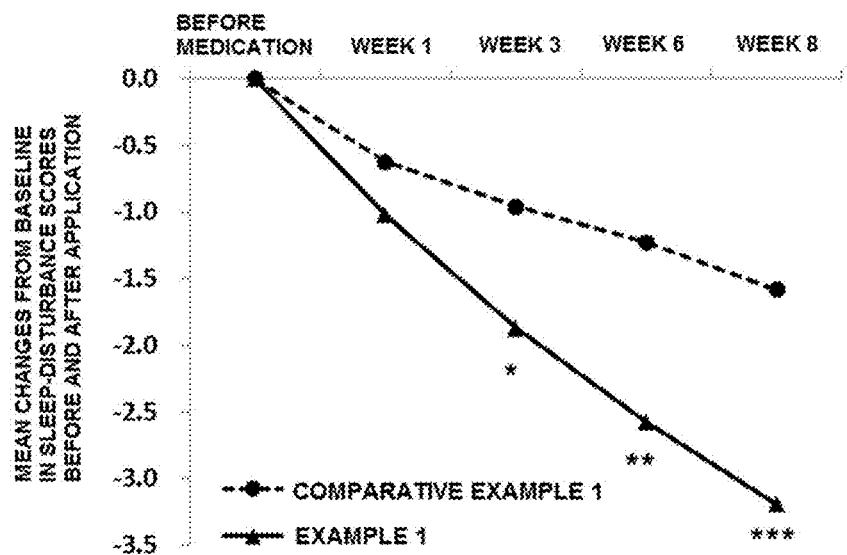
[FIG. 3A]
*p<0.001, p<0.01, *p<0.05 vs. Vehicle; Two sample t-test
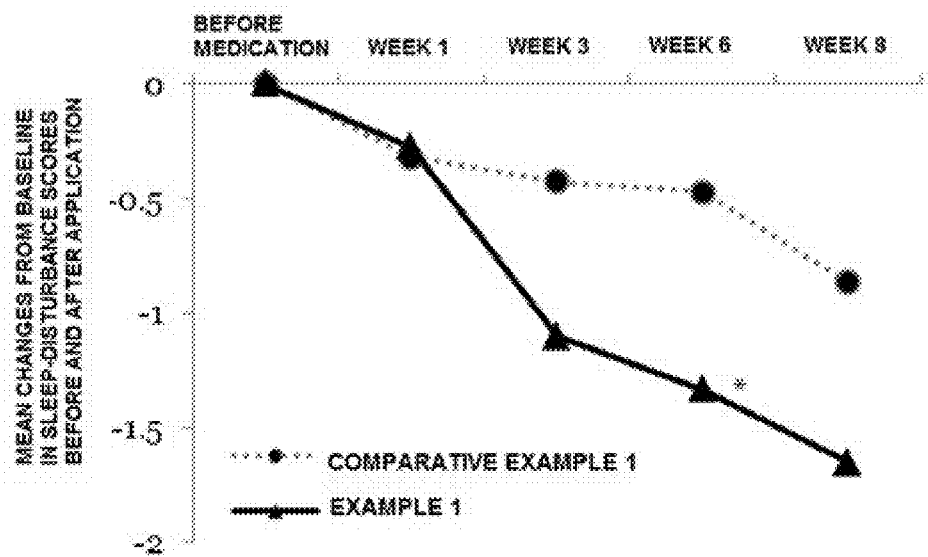
[FIG. 3B]

[FIG. 4A]
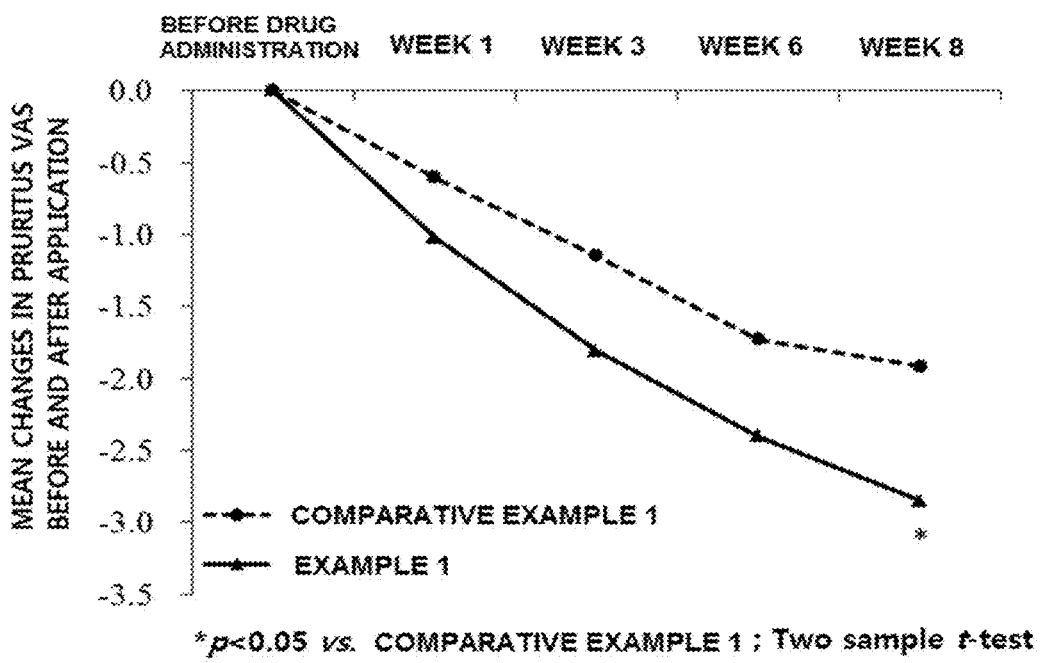
[FIG. 4B]
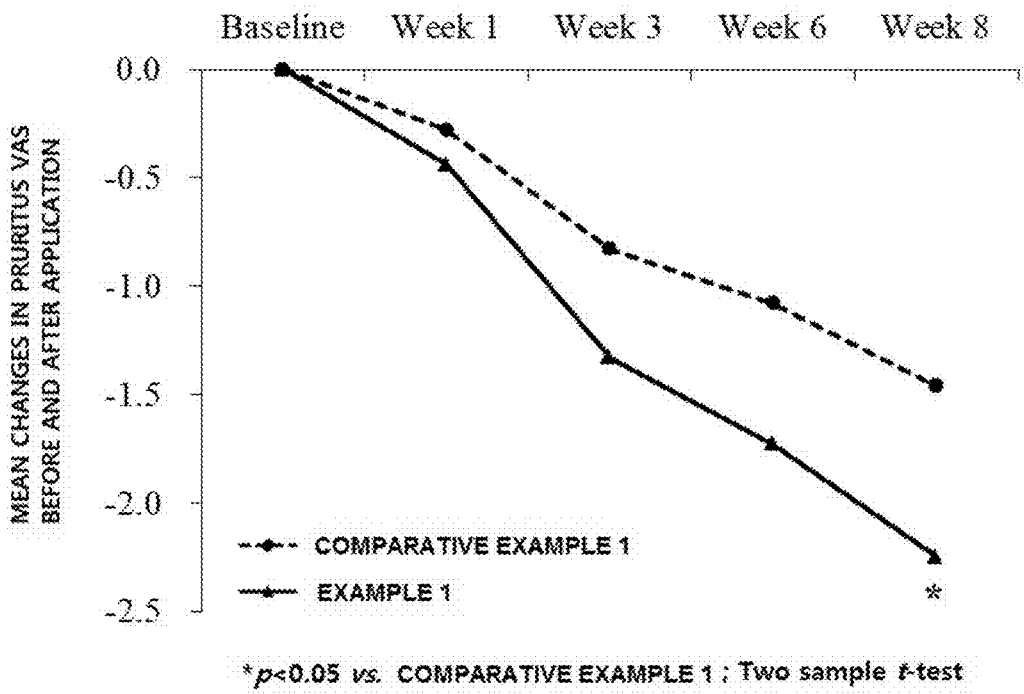

[FIG. 4C]
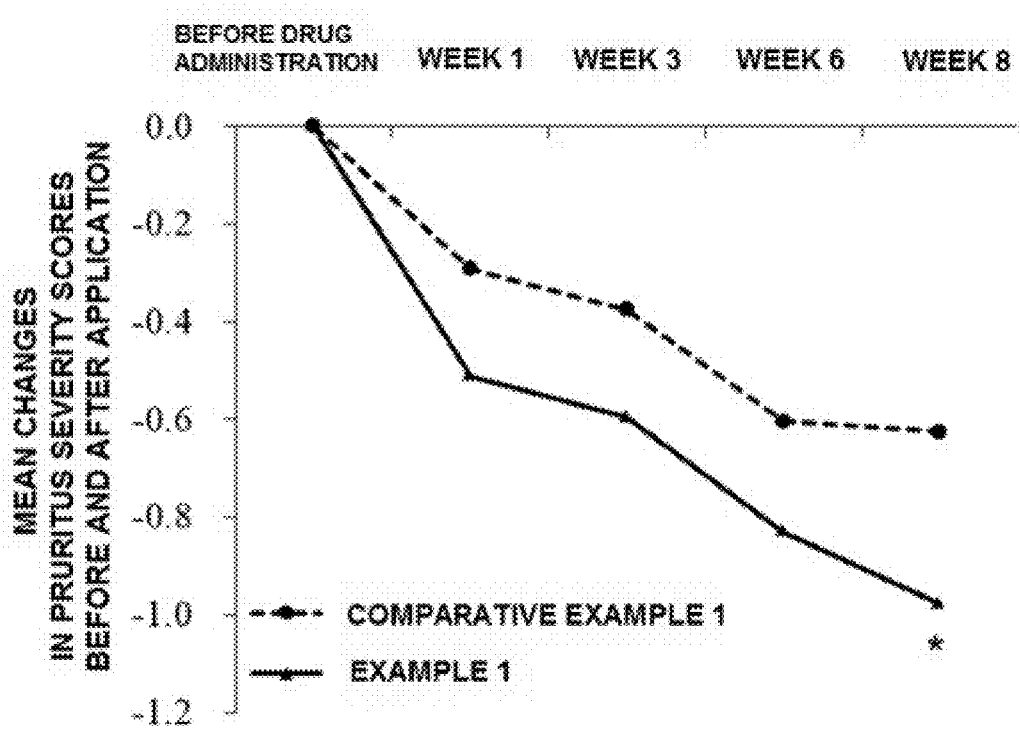
[FIG 5A]
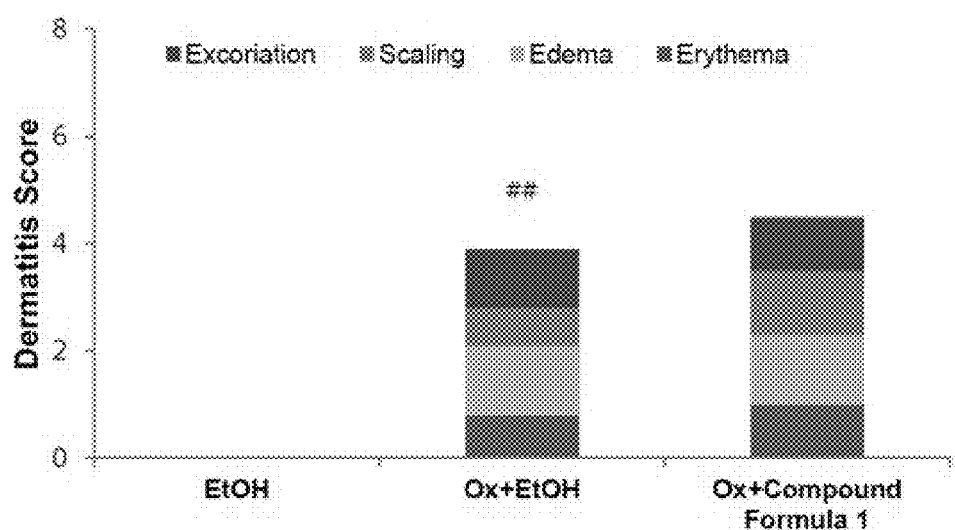

[FIG 5B]
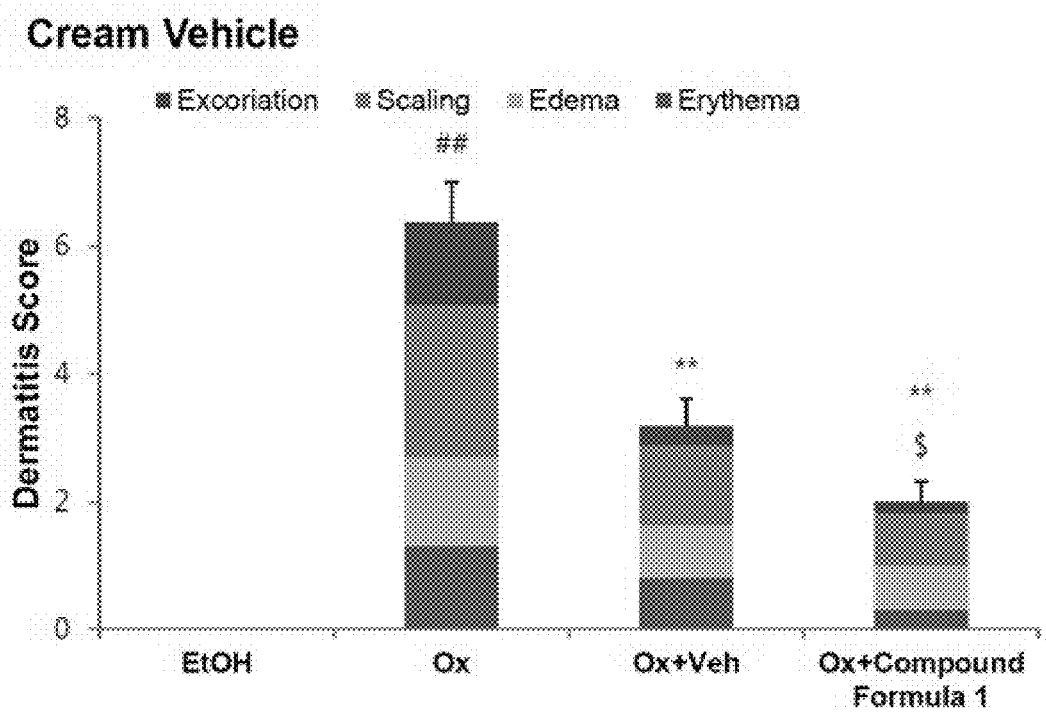
[FIG 6A]
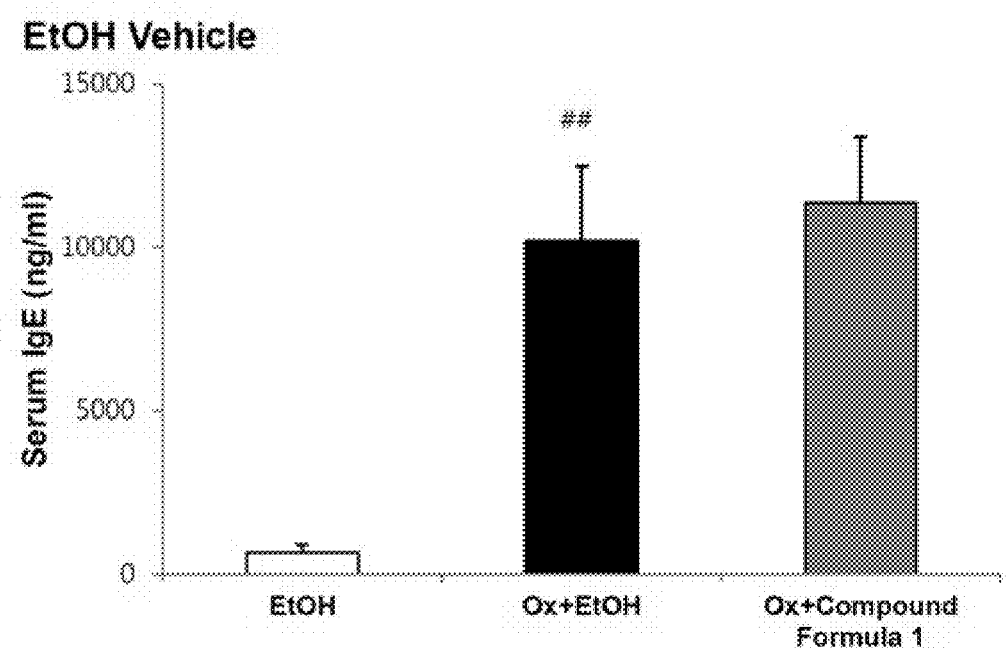

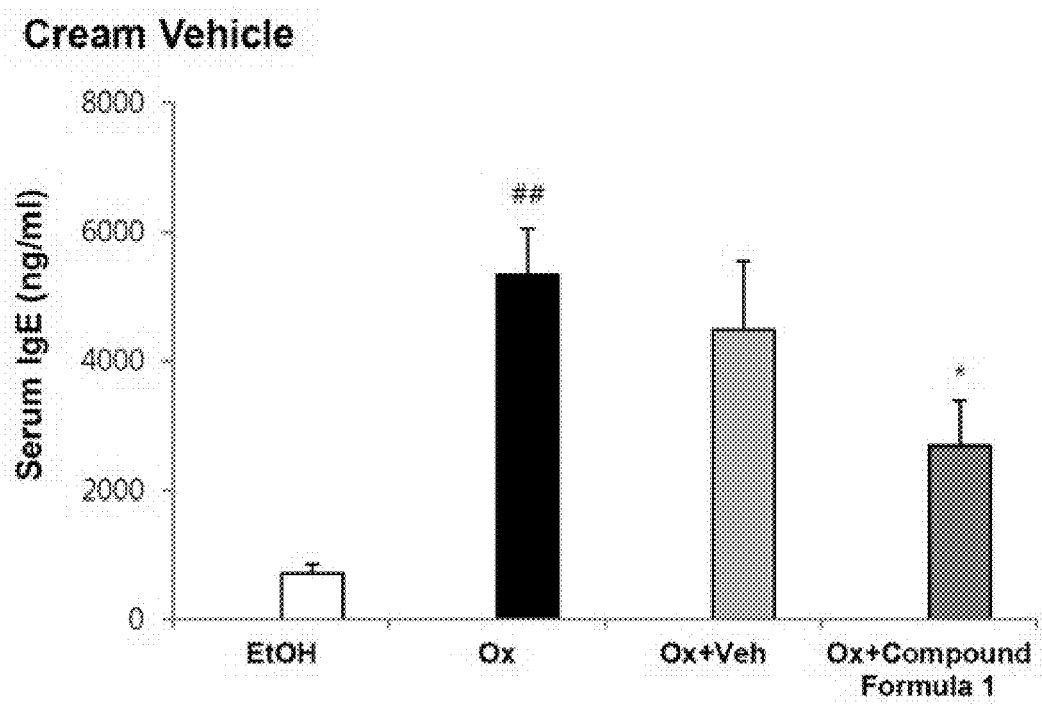

COMPOSITION FOR PREVENTING OR TREATING SLEEP DISORDERS

CROSS-REFERENCE TO RELATED APPLICATION

This application is a continuation-in-part of PCT/KR2018/004330, filed Apr. 13, 2018 which claims the priority from Korean Patent Application No. 10-2017-0110629, filed Aug. 31, 2017, and Korean Patent Application No. 10-2018-0042811 filed Apr. 12, 2018, the contents of each of which are incorporated herein by reference.

BACKGROUND

Technical Field

The present invention relates to a method for preventing or treating sleep disorders using a composition containing a TRPV1 antagonist.

Background Art

Sleep disorder is often found in patients, particularly children, who suffer from atopic dermatitis (AD). Approximately 47 to 60% of the patients suffering from atopic dermatitis develop sleep disorder, which is a main factor that lowers the quality of life of the patients and their families. Sleep disorder has been known to cause unstable nerve function, attention deficit, mood and behavior disorders, and can also have an influence on the patients' heights. No pathological mechanism in which sleep disorder is caused in patients with atopic dermatitis has been clearly elucidated yet. Therapeutic strategies for the pathological mechanism have been mostly established on the basis of the experts' opinions.

The first-generation antihistamines have been most frequently used to modulate sleep disorder. However, antihistamines have limitations in their use because patients can become resistant to the drugs after 4 to 7 days of administration. The use of benzodiazepine, chloral hydrate and clonidine have also been proposed. However, these methods have drawbacks in that no therapeutic effects are sufficiently proved yet. Particularly, the benzodiazepine has problems such as emergence of resistance and more serious sleep disorder when its use is suspended. In addition, the side effects of benzodiazepine, including muscle relaxation, memory impairment, etc., make it burdensome for children to take.

Melatonin has been proposed as a promising therapeutic agent because it serves to encourage sleep and has immunoregulatory and antioxidant effects. However, a safe and effective method capable of modulating sleep disorder in the patients suffering from atopic dermatitis is still needed.

SUMMARY OF THE DISCLOSURE

The present invention provides an unexpectedly and significantly improved method for treating sleep disorder, particularly sleep disorder accompanied with atopic dermatitis, more particularly sleep disorder accompanied with pruritus caused by atopic dermatitis and unexpectedly found that certain compounds such as vanilloid receptor antagonists (belonging to a transient receptor potential vanilloid subfamily; member 1 antagonists, TRPV1 antagonists) may be used to very effectively and safely treat patients having sleep disorder accompanied with atopic dermatitis.

It is therefore an object of the present invention to provide an unexpectedly and significantly improved method for treating sleep disorder, particularly sleep disorder accompanied with atopic dermatitis, more particularly sleep disorder accompanied with pruritus caused by atopic dermatitis with a composition containing TRPV1 antagonist, Compound of Formula 1.

In an embodiment, the present invention relates to provide a pharmaceutical composition for preventing or treating sleep disorder, which includes an effective amount of a compound represented by the following Formula 1 as an active ingredient <Formula 1>

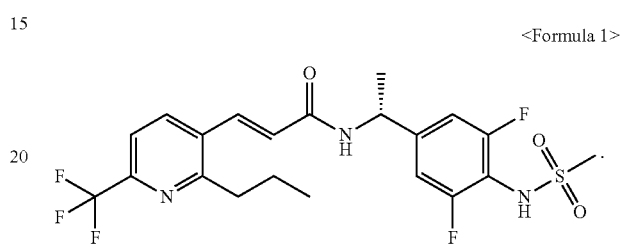

In another embodiment, the present invention to provide a method of preventing or treating sleep disorder accompanied with atopic dermatitis, which includes applying an effective amount of the pharmaceutical composition described above to the skin of a mammal, including a human, in need of such treatment.

Also, the present invention provides the use of the pharmaceutical composition for the preparation of medicines for preventing or treating sleep disorder, particularly sleep disorder accompanied with atopic dermatitis.

BRIEF DESCRIPTION OF THE DRAWINGS

FIGS. 1A and 1B show the results of nonclinical trials on the change in body temperature at the time of transdermal administration according to Experimental Example 1: FIG. 1A is the results of the change in body temperature at the time of transdermal administration of the AMG 517 compound (Amgen) as a TRPV1 antagonist, and FIG. 1B is a graph showing the results of the change in body temperature at the time of transdermal administration of the compound of Formula 1.

FIGS. 2A and 2B show the results of nonclinical trials on the change in body temperature at the time of oral administration according to Experimental Example 1: FIG. 2A is the results of the change in body temperature at the time of oral administration of the AMG 517 compound (Amgen) as a TRPV1 antagonist, and FIG. 2B is a graph showing the results of the change in body temperature at the time of oral administration of the compound of Formula 1.

FIGS. 3A and 3B are graphs illustrating mean changes from baseline in sleep-disorder scores evaluated before and after the application of compositions prepared in Example 1 and Comparative Example 1 (3A: Phase 2 clinical trials, 3B: Phase 3 clinical trials).

FIGS. 4A and 4B are graphs showing the results of the clinical trials on the Mean changes from baseline in Pruritus VAS before and after applying the compositions of Example 1 and Comparative Example 1, and FIG. 4C is a graph showing the Mean changes from baseline in Pruritus severity score before and after applying the compositions of Example 1 and Comparative Example 1 (4A: Phase 2 clinical trials, 4B: Phase 3 clinical trials, 4C: Phase 2 clinical trials).

FIGS. 5A and 5B are the results of an experiment on the change of symptoms of atopic dermatitis when the dosage form of the composition for preventing or treating atopic dermatitis according to the present invention is changed: FIGS. 5A and 5B are graphs showing the degree of atopic symptoms in the case of an ethanol vehicle and a cream vehicle, respectively.

FIGS. 6A and 6B are the results of an experiment on the change in the amount of IgE antibody expression when the dosage form of the composition for preventing or treating atopic dermatitis according to the present invention is changed: FIGS. 6A and 6B are graphs showing the change in the amount of IgE antibody expression in the case of an ethanol vehicle and a cream vehicle, respectively.

DETAILED DESCRIPTION

Hereinafter reference will now be made in detail to various embodiments of the present invention, examples of which are illustrated in the accompanying drawing and described below.

While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention provides a composition capable of preventing or treating sleep disorder when the composition is administered to a patient who suffers from sleep disorder, particularly sleep disorder accompanies with atopic dermatitis. Also, the present invention provides a specific method of administering the composition of the present invention to a patient suffering from sleep disorder, and a method of safely and effectively preventing or treating sleep disorder, which includes adjusting the number of doses of the composition of the present invention.

In general, skin irritations such as excoriation, scaling, edema, or erythema and the expression of the IgE antibody are increased in the patients of atopic dermatitis and the skin irritation results in various complications including sleep disorder. The method of the present invention provides prevention or treatment of the sleep disorder. The skin irritations and the expression of the IgE antibody is also shown to decreased by the method of the present invention.

The composition for preventing or treating sleep disorder, particularly sleep disorder accompanied with atopic dermatitis according to the present invention includes a compound represented by Formula 1 as an active ingredient <Formula 1>

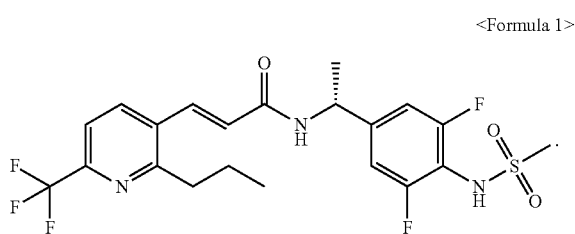 [SMILES: CCCc1nc(C(F)(F)F)ccc1/C=C/C(=O)N[C@H](C)c1cc(F)c(NS(C)(=O)=O)c(F)c1]

The compound represented by Formula 1 is a transient receptor potential vanilloid 1 (TRPV1) antagonist that is useful in treating diseases such as, for example, pain, itching, chronic inflammatory skin diseases, and the like. The compound of Formula 1 according to the present invention, the method of preparing the same, and the vanilloid receptor antagonist activity are specifically disclosed in PCT International Publication No. WO 2008/013414, the disclosure of which is incorporated herein by reference in its entirety.

In the present invention, the compound of Formula 1 includes both a parent compound and a pharmaceutically acceptable salt thereof. Examples of the compound of Formula 1 include (1) acid addition salts formed of inorganic acids or formed of organic acids; or (2) salts formed when acidic protons present in the parent compound is replaced.

As the active ingredient of the composition for preventing or treating sleep disorder, particularly sleep disorder accompanied with atopic dermatitis according to the present invention, the compound of Formula 1 may be included in an amount of 0.1 wt. % or more, 0.5 wt. % or more, 0.8 wt. % or more, and 1.5 wt. % or less, 1.2 wt. % or less, based on the total weight of the composition. When the content of the compound represented by Formula 1 falls within this content range, the maximum prophylactic and/or therapeutic effects on atopic dermatitis may be achieved.

A preferred subject to whom the composition for preventing or treating sleep disorder according to the present invention is administered is a patient who suffers from atopic dermatitis, that is, a patient with sleep disorder.

Specifically, in the present invention, the patient with sleep disorder may be a patient having a visual analogue scale (VAS) score of 3 to 10.

The VAS is a continuous rating scale that may be assessed by asking the patients to score their displeasure with respect to symptoms of sleep disorder. By considering the symptoms in the last three days, a degree of sleep disorder may be quantified as the scores spanning from 0 to 10. In this case, the VAS score of 0 means that a patient has no sleep disorder, and the VAS score of 10 means that a patient suffers from the most serious sleep disorder, that is, never get into sleep.

The composition for preventing or treating sleep disorder, particularly sleep disorder accompanied with atopic dermatitis according to the present invention may be orally or percutaneously administered. Preferably, it is percutaneously, i.e. topically administered.

The composition of the present invention has an excellent therapeutic effect on sleep disorder when simply applied (i.e., percutaneously administered) onto the infected areas or dermatitis in the subject in need of such treatment.

The compound of Formula 1 according to the present invention may have excellent preventive, therapeutic and palliative effects on sleep disorder accompanied with atopic dermatitis when applied to the skin.

Meanwhile, the cause and pathological mechanism of the sleep disorder accompanied with atopic dermatitis, and the relationships therebetween are not sufficiently known. Also, a therapeutic effect on sleep disorder in the patient with atopic dermatitis due to the TRPV1 antagonism, particularly a therapeutic effect on sleep disorder by percutaneous administration of the compound has not been found yet.

The composition of the present invention has an excellent therapeutic effect on sleep disorder even when particularly applied twice a day onto the skin, and has a very excellent therapeutic effect on sleep disorder when generally continuously used for 2 weeks or more, particularly 3 weeks or more, and preferably 3 weeks to 8 weeks.

Also, a single dose of the composition for external use on the skin varies depending on the condition and weight of a patient, the severity of a disease, the type of a composition, a route of administration, and the administration duration. In this case, the dose of the composition, i.e. an effective amount, applied refers to an amount (i.e., a finger-tip unit (FTU); 0.5 g) of a cream containing the compound of Formula 1 that is squeezed in a row to a length of the last knuckle of the patient's index finger, that is, a proper amount of the cream that is applied to an area (i.e., approximately 2% body surface area (BSA)) which is twice the size of the patient's palm. In the case of a patient with a lesion of BSA of 5% and more, the composition for external use may be preferably administered at a dose of 10 mg to 300 mg in consideration of the severity of the patient with sleep disorder accompanying pruritus caused by atopic dermatitis, and the administration method as described above, and may, for example, be properly adjusted and administered in a range of the daily dose in consideration of the size and shape of a lesion, the severity of symptoms, the age of a patient, and the like. In addition, the daily dose may be 5 mg or more, 10 mg or more, 12.5 mg or more, 20 mg or more, 25 mg or more, and 200 mg or less, 175 mg or less, 150 mg or less, 100 mg or less, 87.5 mg or less, but is not limited therein.

The composition for preventing or treating sleep disorder according to the present invention may be particularly prepared into a preparation for external use on skin, and may be preferably prepared into a cream, a gel, a patch, a spray, an ointment, a plaster, a lotion, a liniment, a paste, a cataplasma, a serum, a pack, a powder, an oil, a wax, a spray, a paste, a solution, a suspension, an emulsion, or a soap.

Meanwhile, the composition may further include various known components in a range which does not hinder the effect of the compound represented by Formula 1, depending on desired formulations. According to one exemplary embodiment, the composition may further include additives selected from the group consisting of a carrier, an emulsifying agent, a moisturizing agent, a skin conditioning agent, a surfactant, a chelating agent, an antioxidant, a disinfectant, a stabilizing agent, and any combination thereof.

The carrier may include animal fibers, vegetable fibers, wax, paraffin, starch, tragacanth, cellulose derivatives, polyethylene glycol, silicone, bentonite, silica, talc, zinc oxide, lactose, silica, aluminum hydroxide, calcium silicate, polyamide powder, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, liquid diluents, ethoxylated isostearyl alcohol, suspending agents such as polyoxyethylene sorbitol ester and polyoxyethylene sorbitan ester, microcrystalline cellulose, aluminum metahydroxide, bentonite, agar or tragacanth, aliphatic alcohol sulfate, aliphatic alcohol ether sulfate, sulfosuccinate monoester, isethionate, imidazolinium derivatives, methyl taurate, sarcosinate, fatty acid amide ether sulfate, alkyl amido betaine, aliphatic alcohol, fatty acid triglyceride, fatty acid diethanol amide, vegetable oil, linolic acid derivatives, or ethoxylated glycerol fatty acid ester, but the present invention is not limited thereto.

The moisturizing agent may include glycerin, glyceryl stearate, and the like, but the present invention is not limited thereto.

The skin conditioning agent may include cyclomethicone, dimethicone, and the like, but the present invention is not limited thereto.

The surfactant may include polyoxyethylene-sorbitan-fatty acid esters, polyoxyethylene fatty acid esters, sorbitan fatty acid esters, polyoxyethylene-polyoxypropylene copolymers, cetearyl glucoside, and mono-/di-glycerides, but the present invention is not limited thereto.

The chelating agent may include ethylenediaminetetraacetic acid (EDTA), α-hydroxy fatty acid, lactoferrin, α-hydroxy acid, citric acid, lactic acid, malic acid, bilirubin, biliverdin, and the like, but the present invention is not limited thereto.

The antioxidant may include butylhydroxyanisole, dibutyl hydroxy toluene, or propyl gallate, but the present invention is not limited thereto.

In addition, components that may be mixed in the composition for external use on skin may include a pH control agent, a plasticizing agent, a solubilizing agent, a gelling agent, a binder, an isotonic agent, a soothing agent, a preservative, a dispersing agent, an opacifying agent, an antioxidant, an osmoregulatory agent, an antifoaming agent, a wetting agent, a thickening agent, an adhesive, a masking agent, a coloring agent, a flavoring agent, a film-forming agent, a suspending agent, a volatile restrainer, an absorbent, an oily component, an emolient, an organic and inorganic pigment, an organic powder, a UV absorbent, an alcohol, a blood flow stimulant, a cooling agent, a limiting agent, and the like.

The composition for external use on skin according to the present invention may be preferably in the form of an oil-in-water (O/W) emulsion, which includes:
(1) the compound of Formula 1;
(2) one or more components selected from the group consisting of a cellulose-based polymer and a vinylpyrrolidone-based polymer as the stabilizing agent;
(3) one or more components selected from the group consisting of diethylene glycol monoethylether, polyethylene glycol, 2-pyrrolidone, and dimethyl sulfoxide as a solvent;
(4) water as an aqueous component;
(5) one or more components selected from the group consisting of PEG-30 hydrogenated castor oil, medium-chain triglyceride, cetostearyl alcohol, squalane and cyclomethicone as an oily component;
(6) one or more components selected from the group consisting of a polyoxyethylene-sorbitan-fatty acid ester, a polyoxyethylene fatty acid ester, a sorbitan fatty acid ester, a polyoxyethylene-polyoxypropylene copolymer, a cetearyl glucoside, and a mono-/di-glyceride as the surfactant; and
(7) one or more components selected from the group consisting of xanthan gum, gelatin, gellan gum, carragheenan, and carbomer as the thickening agent.

In the composition of the present invention, the compound of Formula 1 as the drug may be included at a content of 0.1 to 1.5 wt %, based on the total weight of the composition. The cellulose-based polymer or vinylpyrrolidone-based polymer as the stabilizing agent may be included at a content of 1 to 5 wt %, based on the total weight of the composition. The solvent may be included at a content of 5 to 20 wt %, based on the total weight of the composition. The aqueous component may be included at a content of 45 to 90 wt %, based on the total weight of the composition. The oily component may be included at a content of 5 to 30 wt %, the surfactant may be included at a content of 1 to 10 wt %, and the thickening agent may be included at a content of 0.01 to 5 wt %, based on the total weight of the composition.

The composition of the present invention was percutaneously administered twice a day for 8 weeks to patients who have suffered from sleep disorder among the patients with atopic dermatitis who are categorized into mild and moderate groups as will be described below. It was found to be effective in statistically significantly improving sleep disorder in a test group of patents to which a pharmaceutical composition prepared in Example 1 was administered, compared to a placebo group of patients (see Experimental Example 2). From these results, it can be seen that the composition of the present invention including the compound of Formula 1 as the active ingredient may effectively and safely treat sleep disorder, particularly sleep disorder accompanied with atopic dermatitis even when the composition is percutaneously administered.

EXAMPLE 1

Preparation of Pharmaceutical Composition Including Compound of Formula 1 According to the Present Invention A composition for external use on skin in the form of a cream formulation including the compound of Formula 1 was prepared using the components and contents as listed in the following Table 1. Specifically, the oily and aqueous components having the contents as listed in the following Table 1 were first emulsified at 65° C., and a solution of the compound of Formula 1 dissolved in polyethylene glycol (PEG400 commercially available from Merck) which was the base was added thereto. Thereafter, a thickening agent and additives were added thereto, homogenized, and then cooled to 35° C. to prepare a composition for external use on skin in the form of a cream formulation.

COMPARATIVE EXAMPLE 1

Preparation of Placebo Composition (Including No Compound of Formula 1) for Comparison with Example 1

A composition for external use on skin in the form of a cream formulation was prepared in the same manner as in Example 1 using the same components and contents as listed in the following Table 1, except that the compound of Formula 1 was not used.

TABLE 1

| Units: wt % | Components | Example 1 | Comparative Example 1 |
|---|---|---|---|
| Oily components | Medium-chain triglyceride | 4.5 | 4.5 |
| | Cetostearyl alcohol | 3.5 | 3.5 |
| | Cyclomethicone | 4.5 | 4.5 |
| Surfactants | Polysorbate 60 | 1.5 | 1.5 |
| | Mono-/di-glyceride | 1.5 | 1.5 |
| Thickening agent | Carbomer | 0.25 | 0.25 |
| Active ingredient | Compound of Formula 1 | 1 | 0 |
| Aqueous component | Purified water | Balance | Balance |
| Base | PEG 400 | 10 | 10 |
| Stabilizing agent | Hypromellose 2910 | 2.5 | 2.5 |
| Additives | Preservative, Neutralizing agent, Pigment, and Flavor ingagent | Proper amounts | Proper amounts |

FORMULATION EXAMPLE 1

Gel

A gel including the compound of Formula 1 according to the present invention was prepared according to a conventional method using the components and contents as listed in the following Table 2.

TABLE 2

| Components | wt % |
|---|---|
| Compound of Formula 1 | 1 |
| PEG 400 | 10 |
| Hypromellose 2910 | 2 |
| α-ketoglutaric acid | 1.0 |
| Niacinamide | 1.0 |
| β-1,3-glucan | 0.1 |
| Ethylenediamine sodium acetate | 0.05 |
| Glycerin | 5.0 |
| Carboxyvinylpolymer | 0.3 |
| Ethanol | 5.0 |
| Triethanolamine | 0.3 |
| Preservative and Flavoring agent | 0.1 |
| Purified water | Balance |

FORMULATION EXAMPLE 2

Ointment

An ointment including the compound of Formula 1 according to the present invention was prepared according to a conventional method using the components and contents as listed in the following Table 3.

TABLE 3

| Components | wt % |
|---|---|
| Compound of Formula 1 | 1 |
| PEG 400 | 10 |
| Hypromellose 2910 | 2.5 |
| α-ketoglutaric acid | 1.0 |
| Niacinamide | 1.0 |
| β-1,3-glucan | 10.0 |
| Wax | 10.0 |
| Polysorbate | 5.0 |
| PEG-60 hydrogenated castor oil | 2.0 |
| Sorbitan sesquioleate | 0.5 |
| Vaseline | 5.0 |
| Liquid paraffin | 10.0 |
| Squalane | 5.0 |
| Shea butter | 3.0 |
| Caprylic/capric triglyceride | 5.0 |
| Glycerin | 10.0 |
| Propylene glycol | 10.2 |
| Triethanolamine | 0.2 |
| Preservative and Flavoring agent | 0.1 |
| Purified water | Balance |

FORMULATION EXAMPLE 3

Lotion

A lotion including the compound of Formula 1 according to the present invention was prepared according to a conventional method using the components and contents as listed in the following Table 4.

TABLE 4

| Components | wt % |
| --- | --- |
| Compound of Formula 1 | 1 |
| PEG 400 | 10 |
| Hypromellose 2910 | 2 |
| Shea butter | 3.0 |
| Caprylic/capric triglyceride | 5.0 |
| Polysorbate | 3.0 |
| Glycerin | 10.0 |
| Propylene glycol | 10.2 |
| Triethanolamine | 0.2 |
| Preservative and Flavoring agent | 0.1 |
| Purified water | Balance |

EXPERIMENTAL EXAMPLE 1

Comparison of Changes in Body Temperature in Nonclinical Trials by Administration of TRPV1 Antagonist Development of the AMG 517 compound represented by the following Formula 2 as a representative TRPV1 antagonist was discontinued, due to the side effects associated with body temperature during clinical trials for the treatment of toothache by Amgen, a multinational pharmaceutical company. According to Amgen's announcement, it was confirmed that the body temperature is increased by about 1.3° C. in rats at the oral dose of 3 mg/kg, and it is considered that the effective concentration to maximize analgesic efficacy was less than 0.3 mg/kg in rats, and this dose did not significantly raise the issue of side effects and thus clinical trials were proceeded. It was confirmed that oral administration for the treatment of dental pain has been reported to raise body temperature in human up to about 40° C. and resulted in a concentration-dependent side effect of hyperthermia (Gavva et al., 2008. Pain 136, 202-210):

<Formula 2>

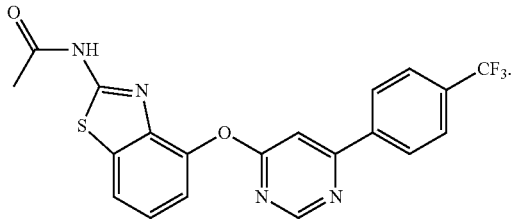

As described above, AMG 517, a representative reference drug as a TRPV1 antagonist, and the compound of Formula 1 of the present invention were tested for the increase in body temperature during transdermal administration. Considering the different drug absorption patterns due to damage to the skin barrier in patients with skin diseases such as atopic dermatitis, after damaging the keratin by tape stripping the skin of the back of experimental animals (C57BL/6 mice), the changes in body temperature were observed at 0, 1, 2, 4, and 6 hours before and after transdermal application with 0.1%, 0.3%, and 1.0% test materials. In this case, as shown in FIG. 1A, it is confirmed that when AMG 517 was applied, a significant concentration-dependent increase in body temperature (~1.59° C.) was observed at 2 hours after administration of all concentrations, as compared with before application. As shown in FIG. 1B, when the compound of Formula 1 was applied, body temperature in the 1.0% dose group was increased only by 2 hours (~0.84° C.) but no concentration dependence was observed.

Meanwhile, when the same drug was orally administered, a concentration-dependent increase in body temperature due to TRPV1 antagonism was observed as expected (see FIGS. 2A and 2B). Specifically, the changes in body temperature of up to 4 hours by administration of 0.03, 0.1 and 0.3 mg/kg of AMG 517 (FIG. 2A), and 3, 10 and 30 mg/kg of compound of Formula 1 (FIG. 2B) were observed in experimental animals (Balb/c mice). Both drugs increased body temperature in a dose—dependent manner, and AMG 517 significantly increased body temperature at a very low dose of 0.03 mg/kg.

In general, the itching of patients with skin diseases such as atopic dermatitis increased when their body temperature is increased, thereby causing a sleep disorder. Thus, it can be seen that the group of transdermal administration of the compound of formula 1 is also effective in improving the sleeping disorder.

EXPERIMENTAL EXAMPLE 2

Clinical Drug Administration According to Types of Composition for External Use on Skin Clinical trials were performed to evaluate safety and efficacy of the compositions for external use on skin prepared in Example 1 and Comparative Example 1.

The clinical trials were conducted as Phase 2 clinical trials and Phase 3 clinical trials for patients diagnosed with atopic dermatitis. Generally, Phase 2 clinical trials are trials for evaluating the efficacy and safety of test drugs in patients to determine the potential as new drugs, optimal dose and use, and to explore therapeutic effects. Phase 3 clinical trials are the largest clinical trials to obtain additional information and corroborating data on the effectiveness of the drugs.

Hereinafter, Phase 2 clinical trials and Phase 3 clinical trials will be described in detail. The experimental groups administered with the compositions for external use on the skin of Example 1 and Comparative Example 1 correspond to the test group(PAC-14028 cream 1.0%) and the placebo group (vehicle cream), respectively.

(1) Phase 2 Clinical Trials

Subjects to which the composition was to be administered were male and female adult patients, aged 19 years to 70 years old, who have been diagnosed with atopic dermatitis based on the Hanifin and Rajka diagnostic criteria and has sleep disorder cause by the atopic dermatitis accompanying pruritus. The patients having eruptions due to mild and moderate atopic dermatitis, which corresponded to an IGA grade of 2 to 3, were subjected to randomized, double-blind, multicenter, and placebo-controlled parallel-design trials.

Specifically, the subjects to which the compositions for external use on the skin of Example 1 and Comparative Example 1 were applied were divided into groups of 48 patients (test group, n=48) and 49 patients (placebo group, n=49) who suffered from sleep disorder cause by the atopic dermatitis accompanying pruritus. The clinical trials were conducted in 19 to 70 year-old male and female patients who had been diagnosed with mild and moderate atopic dermatitis and who had eruption sites having a body surface area (BSA) of 5% or more and an investigator's global assessment (IGA) grade of 2 to 3.

A method of administration was performed by percutaneously applying the composition for external use on the skin twice a day for 8 weeks. The composition was applied onto the skin so that the daily dose of the composition was in a range of approximately 25 to 250 mg/day.

(2) Phase 3 Clinical Trials

Subjects to which the composition was to be administered were male and female adolescent and adult patients, aged 12 years to 70 years old, who have been diagnosed with atopic dermatitis based on the Hanifin and Rajka diagnostic criteria and has sleep disorder cause by the atopic dermatitis accompanying pruritus. The patients having eruptions due to mild and moderate atopic dermatitis, which corresponded to total BSA of 5% to 30% and an IGA grade of 2 (mild) or 3 (moderate), were subjected to randomized, double-blind, multicenter, and placebo-controlled parallel-design trials.

Specifically, the subjects to which the compositions for external use on the skin of Example 1 and Comparative Example 1 were applied were divided into groups of 160 patients (test group, n=160) and 80 patients (placebo group, n=80) who suffered from atopic dermatitis.

Data of the patients were excluded, who did not participate to the end of the Phase 3 clinical trials due to contact disruptions or violated clinical protocols using other drugs. Therefore, the results of phase 3 clinical trials of the following Experimental Examples 2-1 to 2-4 are the results for the test groups (n=153) and the placebo groups (n=78) except the above patients.

A method of administration was performed by percutaneously applying the composition for external use on the skin twice a day for 8 weeks. The composition was applied onto the skin so that the daily dose of the composition was in a range of approximately 25 to 150 mg/day.

EXPERIMENTAL EXAMPLE 2-1

Comparison of Therapeutic Effect of Compositions of Example 1 and Comparative Example 1 on Sleep Disorder Clinical trials were performed on each of the compositions prepared in Example 1 and Comparative Example 1 to determine a change in sleep disorder.

The composition was applied to the patient of the Phase 2 clinical trials and Phase 3 clinical trials and was applied onto the skin. On weeks 1, 3, 6 and 8 of the application, a degree of sleep disorder in which the individual patients felt was evaluated, and a change in sleep-disorder score was calculated therefrom. That is, the sleep-disorder score was evaluated by rating a degree of sleep disorder as grades 0 to 10 on the basis of the severity of symptoms which the patients recalled in the last three days before the evaluation. In this case, the grade 0 means that a patient had "no sleep disorder," and the grade 10 means that a patient suffered from "serious sleep disorder."

FIGS. 3A and 3B are graphs illustrating mean changes from baseline in sleep-disorder scores evaluated before and after the application of compositions prepared in Example 1 and Comparative Example 1 (3A: Phase 2 clinical trials, 3B: Phase 3 clinical trials).

As shown in FIGS. 3A and 3B, it can be seen that the composition of the present invention started to statistically significantly improve sleep disorder from week 3 of the percutaneous administration, and improved sleep disorder by more than two times on the end point (week 8) of treatment, compared to the placebo group to which the composition of Comparative Example 1 was administered.

From the aforementioned results of Experimental Example 21, it can be seen that the composition including the compound of Formula 1 according to the present invention was effectively used to treat sleep disorder in the patients with atopic dermatitis when percutaneously administered.

EXPERIMENTAL EXAMPLE 2-2

Analysis of Therapeutic Success Rate for Atopic Dermatitis Using IGA

In this clinical trial, a therapeutic success rate of the composition for external use on skin to treat atopic dermatitis was analyzed to determine an IGA grade.

In this case, IGA is used to evaluate the severity of atopic dermatitis and a clinical response to therapy on the basis of a 6-point scale spanning from 0 (clear symptoms) to 5 (very severe symptoms).

The IGA grade of 0 to 1 was considered to be a success of therapy, and the IGA grade of 2 to 5 was considered to be a failure of therapy.

The following Table 5 shows therapeutic success rates for atopic dermatitis at the time point of week 8 after administration of the compositions for external use on the skin of Comparative Example 1 and Example 1.

TABLE 5

| | Therapeutic success rate (IGA grade) | Example 1 (test group, n = 48) | Comparative Example 1 (placebo group, n = 49) | p-value |
|---|---|---|---|---|
| Phase 2 clinical trials | Success (IGA 0 to 1) | 57.45% | 14.58% | 0.0001 (Comparative Example 1, vs. placebo group) |

| | Therapeutic success rate (IGA grade) | Example 1 (test group, n = 153) | Comparative Example 1 (placebo group, n = 78) | p-value |
|---|---|---|---|---|
| Phase 3 clinical trials | Success (IGA 0 to 1) | 35.95% | 12.82% | 0.0002 (Comparative Example 1, vs. placebo group) |

Referring the Table 5, it can be seen that the therapeutic success rates for atopic dermatitis at the time point of week 8 after administration of the compositions for external use on the skin of Comparative Example 1 and Example 1 were 8.33% and 61.54% in the Phase 2 pediatric clinical trials, 14.58% and 57.45% in the Phase 2 clinical trials, and 12.82% and 35.95% in the Phase 3 clinical trials, respectively, indicating that the composition for external use on the skin of the present invention had a statistically significant and excellent therapeutic effect.

In addition, it can be seen that the composition of Example 1 is effective for improving sleep disorder, which is caused by pruritus accompanied when increasing in body temperature of the patients with atopic dermatitis.

EXPERIMENTAL EXAMPLE 2-3

Therapeutic Effect for Sleep Disorder by Improvement of Pruritus

On weeks 8 from a baseline after the application of the compositions for external use on the skin, in the Phase 2 patients and the Phase 3 patients, degrees of pruritus in which the individual patients felt when the composition was applied were evaluated as a visual analogue scale (VAS) and measured mean change in pruritus VAS.

FIG. 4A is a graph showing the results of the Phase 2 clinical trials on Mean changes from baseline in Pruritus VAS before and after the application of the compositions of Example 1 and Comparative Example 1, and FIG. 4B is a graph showing the results of the Phase 3 clinical trials on Mean changes from baseline in Pruritus VAS before and after the application of the compositions of Example 1 and Comparative Example 1.

FIG. 4C is a graph showing the results of the Phase 2 clinical trials on Mean changes from baseline in Pruritus severity score before and after the application of the compositions of Example 1 and Comparative Example 1. In this case, the evaluation criteria of the Pruritus severity score are as shown in Table 6 below, and the intensity of the pruritus and scratching behavior during the last 24 hours was directly assessed by the patient on a 4-point scale.

TABLE 6

| | | Pruritus severity score |
|---|---|---|
| Score | Grade | Description |
| 0 | Absent | No pruritus |
| 1 | Mild | Occasional slight pruritus & scratching |
| 2 | Moderate | Constant or intermittent pruritus & scratching, causing no disturbing sleep |
| 3 | Severe | Bothersome pruritus & scratching with the difficulty in daily life, causing disturbing sleep |

As listed in FIGS. 4A, 4B and 4C, it can be seen that the composition of the present invention had an effect of statistically significantly improving pruritus from the first week of drug administration, compared to the placebo composition. Also, after a placebo or a test drug was administered to the patients, the efficacy of a change in pruritus severity scores was evaluated. As a result, it can be seen the composition of the present invention had an effect of significantly improving pruritus, which was similar to that in the VAS evaluation. The pruritus severity scores were measured by allowing the patients to directly evaluate pruritus and scratching intensity for the scores on the 4-point scale for 24 hours after the placebo or test drug was administered to the patients, as listed in the following tables. From the above results, it can be seen that the composition including the compound of Formula 1 of the present invention can be used to effectively treat pruritus, which is a major symptom in patients with atopic dermatitis by percutaneous administration.

EXPERIMENTAL EXAMPLE 2-4

Comparison of Changes in Body Temperature After Percutaneous Administration

Next, the difference in body temperature before application (Baseline) and after 4-week application (children)/8-week application (adolescents/adults)(End of study) of the composition for external use on the skin was used to calculate the change in body temperature of patients with sleep disorder caused by atopic dermatitis, as listed in Table 7 below.

TABLE 7

| | Body temperature (° C.) | Example 1 (n = 48) | Comparative Example 1 (n = 49) |
|---|---|---|---|
| Phase 2 clinical trials | Baseline | 36.50 ± 0.19 | 36.48 ± 0.19 |
| | End of study | 36.51 ± 0.24 | 36.52 ± 0.20 |
| | Change | 0.02 ± 0.16 | 0.06 ± 0.14 |

TABLE 7-continued

| | Body temperature (° C.) | Example 1 (n = 153) | Comparative Example 1 (n = 78) |
|---|---|---|---|
| Phase 3 clinical trials | Baseline | 36.49 ± 0.23 | 36.42 ± 0.22 |
| | End of study | 36.48 ± 0.24 | 36.42 ± 0.24 |
| | Change | −0.01 ± 0.28 | 0.00 ± 0.24 |

Referring to Table 7, it can be seen that, when the composition of Example 1 of the present invention was percutaneously applied to the subjects to which the composition was to be administered using the administration method, in patients of 12 years old to 70 years old, no clinically significant changes in body temperature was observed with respect to elevated body temperature, which is a common side effect of conventional TRPV1 antagonists.

In addition, it can be seen that the composition of Example 1 is effective for improving sleep disorder from the results of the clinical trials regarding changes in body temperature.

EXPERIMENTAL EXAMPLE 3

Experiment on the Efficacy of Treatment of Atopic Dermatitis According to the Form of the Formulation Experiments were conducted to observe changes in atopic dermatitis symptoms and changes in the expression level of IgE antibodies that cause atopic dermatitis when the dosage form of the composition for preventing or treating atopic dermatitis is changed.

For nude mouse with atopic dermatitis induced by oxazolone (Ox), ethanol vehicle vehicle were applied once a day to the neck area for 14 days and cream vehicle were applied twice a day to the neck area for 14 days to measure the degree of atopic dermatitis symptoms and the amount of IgE antibody expression. In this case, symptoms of measured atopic dermatitis are excoriation, scaling, edema and erythema.

FIG. 5A is a result of measurement of symptoms of atopic dermatitis after application of ethanol vehicle to nude mouse having atopic dermatitis induced by oxazolone. Specifically, as results of ethanol application (Ox+EtOH), and of the application of ethanol containing 1% by weight of compound of Formula 1 (Ox+Compound of Formula 1), it can be seen that in the case of the ethanol vehicle, the symptoms of atopic dermatitis are not alleviated even when the compound of formula (1) is contained.

FIG. 5B is a result of measurement of symptoms of atopic dermatitis after application of cream vehicle to nude mouse having atopic dermatitis induced by oxazolone. Specifically, as results of the composition of Comparative Example 1 (Ox+Veh) of a cream formulation, a control group (Ox) which does not contain the compound of Formula 1, and of the composition of Example 1 of a cream formulation which contains 1% by weight of the compound of Formula 1 (Ox+Compound of Formula 1), it can be seen that in the case of the cream vehicle, symptoms of atopic dermatitis are remarkably alleviated when the compound of Formula 1 is applied to the composition of Example 1.

FIG. 6A is a result of measurement of the amount of serum IgE antibody expression (Serum IgE) after application of ethanol vehicle to nude mouse having atopic dermatitis induced by oxazolone. Specifically, as results of ethanol application (Ox+EtOH), and of the application of ethanol containing 1% by weight of compound of Formula 1 (Ox+Compound of Formula 1), it can be seen that in the case of the ethanol vehicle, the amount of serum IgE antibody expression is increased rather when the compound of Formula (1) is contained.

FIG. 6B is a result of measurement of the amount of serum IgE antibody expression (Serum IgE) after application of cream vehicle to nude mouse having atopic dermatitis induced by oxazolone. Specifically, as results of the composition of Comparative Example 1 (Ox+Veh) of a cream formulation, a control group (Ox), which does not contain the compound of Formula 1, and of the composition of Example 1 of a cream formulation which contains 1% by weight of the compound of Formula 1 (Ox+Compound of Formula 1), it can be seen that in the case of the cream vehicle, the amount of serum IgE antibody expression is decreased when the compound of Formula 1 is applied to the composition of Example 1.

In general, skin irritations such as excoriation, scaling, edema, or erythema and the expression of the IgE antibody are increased in the patients of atopic dermatitis and the skin irritation results in various complications including sleep disorder. The cream formulation comprising 1 wt % of the Compound of Formula 1 decreases provides prevention or treatment of the sleep disorder by decreasing the skin irritations and the expression of the IgE antibody.

Hereinbefore, the present invention has been described with reference to limited examples and drawings, however, the present invention is not limited thereto, and by those skilled in the art, various changes and modifications may be made within technological ideas of the present invention and the range of equivalents of the attached claims.

What is claimed is:

1. A method of preventing or treating a sleep disorder in a subject, comprising administering an effective amount of the compound of Formula 1 to a subject in need thereof:

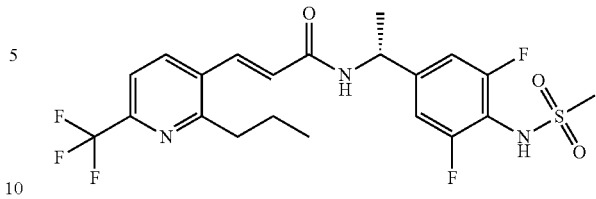

<Formula 1> wherein the sleep disorder is accompanied with pruritus caused by atopic dermatitis.

2. The method of claim 1, wherein the subject is a patient with atopic dermatitis who has a visual analogue scale (VAS) score of 3 to 10.

3. The method of claim 1, wherein the compound is applied onto the skin of the subject as part of a topical composition.

4. The method of claim 3, wherein the topical composition is applied onto the skin twice a day.

5. The method of claim 3, wherein the topical composition is applied onto the skin twice a day for 3 weeks to 8 weeks.

6. The method of claim 3, wherein compound is administered as part of a composition and said composition comprises 0.1 to 1.5 wt % of the compound.

7. The method of claim 3, wherein the composition is in the form of a cream, a gel, a patch, a spray, an ointment, a plaster, a lotion, a liniment, a paste, or a cataplasma.

8. The method of claim 3, wherein the amount of the compound of Formula 1 administered is from 10 to about 300 mg.

* * * * *